United States Patent
Arba Mosquera

(10) Patent No.: US 12,285,363 B2
(45) Date of Patent: Apr. 29, 2025

(54) METHOD FOR CONTROLLING AN EYE SURGICAL LASER AND TREATMENT APPARATUS

(71) Applicant: SCHWIND eye-tech-solutions GmbH, Kleinostheim (DE)

(72) Inventor: Samuel Arba Mosquera, Aschaffenburg (DE)

(73) Assignee: SCHWIND eye-tech-solutions GmbH, Kleinostheim (DE)

( * ) Notice: Subject to any disclaimer, the term of this patent is extended or adjusted under 35 U.S.C. 154(b) by 594 days.

(21) Appl. No.: 17/546,192

(22) Filed: Dec. 9, 2021

(65) Prior Publication Data

US 2022/0183884 A1    Jun. 16, 2022

(30) Foreign Application Priority Data

Dec. 11, 2020    (DE) .................... 10 2020 133 189.4

(51) Int. Cl.
*A61F 9/008*    (2006.01)

(52) U.S. Cl.
CPC ...... *A61F 9/00825* (2013.01); *A61F 9/00802* (2013.01)

(58) Field of Classification Search
CPC .................. A61F 9/00825; A61F 9/00802
See application file for complete search history.

(56) References Cited

U.S. PATENT DOCUMENTS

| | | | |
|---|---|---|---|
| 9,474,647 B2 | 10/2016 | Bischoff et al. | |
| 11,602,457 B2 * | 3/2023 | Bischoff | A61F 9/00804 |
| 2004/0243112 A1 * | 12/2004 | Bendett | A61F 9/00827 606/5 |
| 2014/0364840 A1 * | 12/2014 | Donitzky | A61F 9/008 606/4 |

FOREIGN PATENT DOCUMENTS

| | | |
|---|---|---|
| CN | 103889375 A | 6/2014 |
| DE | 102012018421 A1 | 3/2014 |
| EP | 1631223 B1 | 7/2013 |
| WO | 2016049442 A1 | 3/2016 |

OTHER PUBLICATIONS

Notification of the First Office Action issued Oct. 27, 2023 in Chinese Appl. No. 202111508186.8.

* cited by examiner

*Primary Examiner* — Lynsey C Eiseman
*Assistant Examiner* — Skylar Lindsey Christianson
(74) *Attorney, Agent, or Firm* — MEDLER FERRO WOODHOUSE & MILLS PLLC

(57) ABSTRACT

A method is disclosed for controlling an eye surgical laser of a treatment apparatus for the separation of a volume body with a predefined posterior interface and a predefined anterior interface from a human or animal cornea. The method includes controlling the laser with a control device of the treatment apparatus such that it emits pulsed laser pulses in a shot sequence in a predefined pattern into the cornea. The interfaces of the volume body to be separated are defined by the predefined pattern and the interfaces are generated by means of an interaction of the individual laser pulses with the cornea by the generation of a plurality of cavitation bubbles. An arc length of the anterior interface and an arc length of the posterior interface are generated of equal length in all radial directions by at least one indentation in one of the interfaces.

20 Claims, 3 Drawing Sheets

METHOD FOR CONTROLLING AN EYE SURGICAL LASER AND TREATMENT APPARATUS

FIELD

The invention relates to a method for performing a surgical procedure on a human or animal cornea and to a method for controlling an eye surgical laser of a treatment apparatus for the separation of a volume body with a predefined posterior interface and a predefined anterior interface from a human or animal cornea. Further, the invention relates to a treatment apparatus with a control device, to a computer program as well as to a computer-readable medium.

BACKGROUND

Opacities and scars within the cornea, which can arise by inflammations, injuries or native diseases, impair the sight. In particular in case that these pathological and/or unnaturally altered areas of the cornea are located in the axis of vision of the eye, clear sight is considerably disturbed. Visual disorders also often occur, which can result in a considerable restriction of the sight, for example hyperopia or myopia. Hereto, different laser methods by means of corresponding treatment apparatuses are given from the prior art, which can separate a volume body from the cornea and thus can improve the sight for a patient. This laser method is in particular invasive procedures such that it is of particular advantage for the patient if the procedure is performed in a time as short as possible and to a particularly efficient extent.

In removing a volume body, in particular a lenticule, from the cornea, posterior and anterior interfaces are usually defined, which together form the volume body. Therein, it can occur that the arc lengths of the interfaces due to the planned treatment are differently long, whereby wrinkles, superpositions as well as stresses can arise in the treated cornea after removing the volume body, whereby longer recovery times for the treated cornea can occur.

SUMMARY

It is the object of the present invention to provide a method, a treatment apparatus, a computer program as well as a computer-readable medium, by means of which a treatment for a cornea can be performed in improved manner.

This object is solved by a method, a treatment apparatus, a control device, a computer program as well as a computer-readable medium according to the independent claims. Advantageous configurations with convenient developments of the invention are specified in the respective dependent claims, wherein advantageous configurations of the method are to be regarded as advantageous configurations of the treatment apparatus, of the control device, of the computer program and of the computer-readable medium and vice versa.

An aspect of the invention relates to a method for performing a surgical procedure on a human or animal cornea for the separation of a volume body from the cornea and to a method for controlling an eye surgical laser of a treatment apparatus for the separation of a volume body with a predefined posterior interface and a predefined anterior interface from a human or animal cornea. Controlling the laser by means of a control device of the treatment apparatus is effected such that it emits pulsed laser pulses in a shot sequence in a predefined pattern into the cornea, wherein the interfaces of the volume body to be separated are defined by the predefined pattern and the interfaces are generated by means of an interaction of the individual laser pulses with the cornea by generating a plurality of cavitation bubbles, wherein an arc length of the anterior interface in radial direction and an arc length of the posterior interface in radial direction are generated of equal length in all radial directions by means of at least one indentation in one of the interfaces.

In other words, the eye surgical laser is controlled such that the arc lengths of the anterior and posterior interfaces are of equal length viewed in a radial direction of the eye. Hereto, in order to elongate a shorter arc length, an indentation can be generated in one of the two interfaces, wherein the length of the respective interface can be adapted by the additional path, which arises by the indentation. Thus, equally long arc lengths arise. A deviation, in particular an elongation, from the progression of the respective interface, which are generated by the cavitation bubbles, is meant by the indentation, wherein the elongation is preferably generated in a partial area of one of the two interfaces by a change of the curve progression. In particular, the curve progression of one of the two interfaces can have an indentation or bump or groove, which is substantially bulged in the direction of an optical axis, preferably concavely bulged viewed from the direction of the patient, wherein the bulge of the interfaces is usually convex viewed from the direction of the patient. Preferably, the indentation can be arranged in the cornea such that the two interfaces are of equal length in all radial directions. By the invention, the advantage arises that wrinkles and superpositions, which can arise by differently long interfaces, can be compensated for, which avoids unintended stresses in the cornea. Thus a gentler treatment can be achieved and the cornea, in particular the epithelial tissue, furthermore has to less severely adapt to the new situation after a treatment, which overall results in an improvement of the treatment.

The invention also includes configurations, by which additional advantages arise.

In an advantageous form of configuration, it is provided that the at least one indentation is generated at a radially viewed outer part of the volume body, in particular in radially circumferential manner. In other words, the indentation can be generated rotationally symmetrically around a central point of the volume body in an outer part of the volume body. Thus, the indentation is in particular not arranged centrally in the volume body, which for example is to be removed for visual disorder correction, whereby sight restricting effects due to the indentation can be reduced or avoided. By means of the radially circumferential indentation around the volume body, the arc length of the respective interface can be adapted in particularly simple manner.

In a further form of configuration, it is provided that the volume body comprises an optical zone and a transition zone, wherein the at least one indentation is arranged in the transition zone. The optical zone can be a correction area with optical effect for correcting an imaging error or a visual disorder of the cornea and the transition zone can usually be provided for providing a gentle transition from the optical zone into the untreated cornea. Herein, it is preferably provided that the indentation is arranged in the transition zone to compensate for a length difference between the anterior and the posterior arc length, which can for example arise by different radii of curvature of the interfaces in the optical zone. Hereby, the advantage arises that the indentation for compensating for the length differences is not arranged in the area with optical effect, but in the area, which is provided for a gentle transition into the untreated cornea anyway.

It is further advantageous that if the separation of the volume body is performed for myopia correction, the at least one indentation is generated in the posterior interface. Myopia correction is a correction of myopia, thus nearsightedness of the eye, in which objects farther away are presented blurred. In myopia correction, the curvature of the posterior interface is usually flatter than that of the anterior interface. The length difference arising thereby, in particular of the shorter posterior interface, can thus be compensated for by the indentation in the posterior interface, wherein the indentation is preferably arranged in the transition zone. Here, anterior and posterior means that first the anterior interface and subsequently the posterior interface are arranged viewed from outside into the cornea in the direction of the optical axis of the eye. Hereby, the advantage arises that in myopia correction, in which the arc length of the posterior interface is usually shorter, the arc lengths can be compensated for by the indentation.

Further, it has proven advantageous that if the separation of the volume body is performed for hyperopia correction, the at least one indentation is generated in the anterior interface. Hyperopia correction is a correction of hyperopia, thus farsightedness of the eye, in which near objects are presented blurred. In hyperopia correction, the anterior interface can be flatter than the posterior interface, whereby the arc lengths of the interfaces are differently long. In particular, the anterior interface can be shorter by the flatter progression, wherein this length difference of the arc lengths can be compensated for by means of the indentation in the anterior interface.

It is further advantageous that, if the separation of the volume body is performed for an asymmetric correction, in particular astigmatism correction, the respective indentation is generated optionally in the anterior or posterior interface for a respective meridian of the volume body depending on the asymmetric correction. In other words, in asymmetric corrections of the cornea, in particular in astigmatism correction, a respective meridian of the volume body can be differently corrected, which results in either flatter posterior or anterior interfaces depending on the meridian. A correction of imaging errors of the eye is meant by asymmetric correction, which for example arise by a distorted cornea. For example, in case of astigmatism, a perpendicular axis of the cornea can be more severely curved than a horizontal axis or vice versa. Further imaging errors, which can arise by an asymmetry of the cornea, for example include spherical aberrations or a coma. If the cornea is assumed as a hemisphere, a respective arc length from the center or tip of the hemisphere up to a respective edge is meant by meridian, comparable to a longitude of the earth. Since either the posterior or the anterior interface can be shorter according to meridian, the indentation can optionally be generated in that interface, which is shorter, to generate the interfaces equally long in all radial directions. Thus, an improved treatment result can also be achieved in asymmetric correction.

Furthermore, it has proven advantageous that the indentation is provided with a direction of curvature opposite to the curvature of the anterior and/or posterior interface, in particular in posterior direction. Usually, the directions of curvature of the anterior and posterior interface are convexly oriented viewed from the direction of the patient, thus in the same direction of curvature as the cornea. The indentation for elongating one of the interfaces can preferably have an opposite direction of curvature, thus be concave. Hereby, the indentation can be generated in particularly simple manner without too severely influencing the shape of the interfaces and the resulting cornea.

A second aspect of the present invention relates to a control device, which is configured to perform one of the above described methods. The above cited advantages arise. The control device can for example be configured as a control chip, control appliance or application program ("app"). The control device can preferably comprise a processor device and/or a data storage. An appliance or an appliance component for electronic data processing is understood by a processor device. For example, the processor device can comprise at least one microcontroller and/or at least one microprocessor. Preferably, a program code for performing the method according to the invention can be stored on the optional data storage. The program code can then be configured, upon execution by the processor device, to cause the control device to perform one of the above described embodiments of one or both methods according to the invention.

A third aspect of the present invention relates to a treatment apparatus with at least one eye surgical laser for the separation of a tissue predefined by the control data, in particular of a corneal volume with predefined interfaces of a human or animal eye by means of photodisruption and/or photoablation, and at least one control device for the laser or lasers, which is formed to execute the steps of the method according to the first aspect of the invention. The treatment apparatus according to the invention allows that the disadvantages occurring in the use of usual ablative treatment apparatuses are reliably reduced or even avoided.

In a further advantageous configuration of the treatment apparatus according to the invention, the laser can be suitable to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kilohertz (kHz), preferably between 100 kHz and 100 megahertz (MHz). Such a femtosecond laser is particularly well suitable for removing tissue within the cornea. The use of photodisruptive and/or photoablative lasers in the method according to the invention additionally has the advantage that the irradiation of the cornea does not have to be effected in a wavelength range below 300 nm. This range is subsumed by the term "deep ultraviolet" in the laser technology. Thereby, it is advantageously avoided that an unintended damage to the cornea is effected by these very short-wavelength and high-energy beams. Photodisruptive lasers of the type used here usually input pulsed laser radiation with a pulse duration between 1 fs and 1 ns into the corneal tissue. Thereby, the power density of the respective laser pulse required for the optical breakthrough can be spatially narrowly limited such that a high incision accuracy in the generation of the interfaces is allowed. In particular, the range between 700 nm and 780 nm can also be selected as the wavelength range.

In further advantageous configurations of the treatment apparatus according to the invention, the control device can comprise at least one storage device for at least temporary storage of at least one control dataset, wherein the control dataset or datasets include(s) control data for positioning and/or for focusing individual laser pulses in the cornea; and can comprise at least one beam device for beam guidance and/or beam shaping and/or beam deflection and/or beam focusing of a laser beam of the laser. Therein, the mentioned control dataset includes the control data determined in the method for removing the tissue.

Further features and the advantages thereof can be taken from the descriptions of the first inventive aspect, wherein advantageous configurations of each inventive aspect are to be regarded as advantageous configurations of the respectively other inventive aspect.

A fourth aspect of the invention relates to a computer program including commands, which cause the treatment apparatus according to the third inventive aspect to execute the method steps according to the first inventive aspect and/or the method steps according to the second inventive aspect.

A fifth aspect of the invention relates to a computer-readable medium, on which the computer program according to the fourth inventive aspect is stored. Further features and the advantages thereof can be taken from the descriptions of the first to fourth inventive aspects, wherein advantageous configurations of each inventive aspect are to be regarded as advantageous configurations of the respectively other inventive aspect.

BRIEF DESCRIPTION OF DRAWINGS

Further features of the invention are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

In the figures, identical or functionally identical elements are provided with the same reference characters.

DETAILED DESCRIPTION

Figure 1:
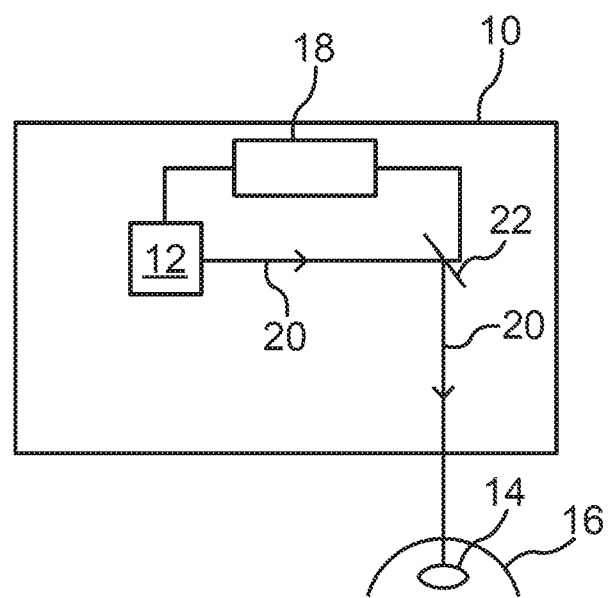
FIG. 1 is a schematic representation of a treatment apparatus according to the invention according to an exemplary embodiment.

FIG. 1 shows a schematic representation of a treatment apparatus 10 with an eye surgical laser 12 for the removal of a volume body 14 from a human or animal cornea 16 by means of photodisruption and/or photoablation. For example, the volume body 14 can be separated from a cornea 16 of an eye by the eye surgical laser 12 for correcting a visual disorder. A predefined pattern for removing the volume body 14 can be provided by a control device 18, in particular in the form of control data, such that the laser 12 emits pulsed laser pulses in a pattern predefined by the control data into the cornea 16 of the eye to form an anterior interface and a posterior interface, which together result in the volume body 14. Alternatively, the control device 18 can be a control device 18 external with respect to the treatment apparatus 10.

Furthermore, FIG. 1 shows that the laser beam 20 generated by the laser 12 can be deflected towards the cornea 16 by means of a beam deflection device 22, such as for example a rotation scanner, to separate the volume body 14. The beam deflection device 22 can also be controlled by the control device 18 to remove the volume body 14.

Preferably, the illustrated laser 12 can be a photodisruptive and/or photoablative laser, which is formed to emit laser pulses in a wavelength range between 300 nanometers and 1400 nanometers, preferably between 700 nanometers and 1200 nanometers, at a respective pulse duration between 1 femtosecond and 1 nanosecond, preferably between 10 femtoseconds and 10 picoseconds, and a repetition frequency of greater than 10 kilohertz, preferably between 100 kilohertz and 100 megahertz. Optionally, the control device 18 additionally comprises a storage device (not illustrated) for at least temporary storage of at least one control dataset, wherein the control dataset or datasets include(s) control data for positioning and/or for focusing individual laser pulses in the cornea.

Figure 2:
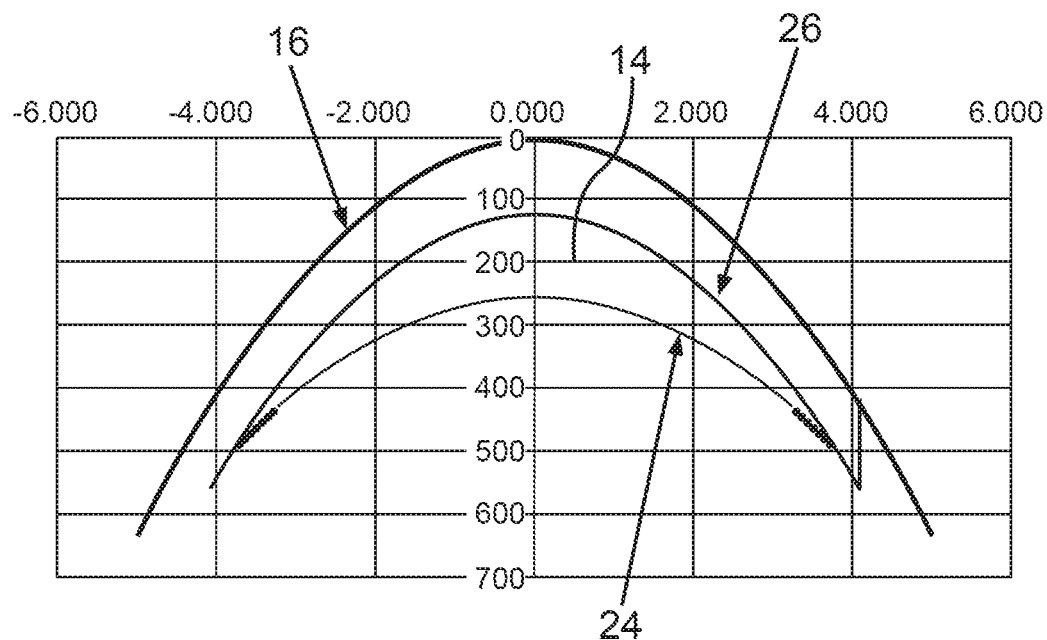
FIG. 2 is a schematic representation of a cornea with an anterior and posterior interface in myopia correction.

In FIG. 2, a cornea 16 with a volume body 14 is illustrated, as it is usually generated in myopia correction. Here, a schematic lateral cross-section through the cornea 16 is in particular illustrated, wherein the posterior interface 24 is formed flatter than the anterior interface 26. This results in the fact that an arc length of the posterior interface 24 is shorter than an arc length of the anterior interface 26, which can result in stresses and superposition problems in the cornea 16.

Figure 3:
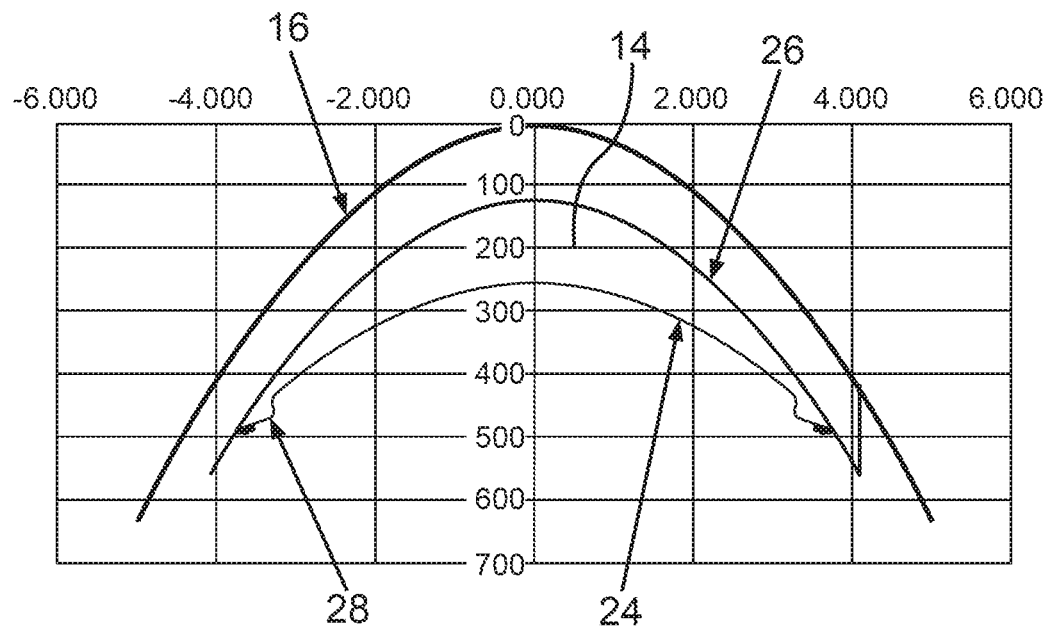
FIG. 3 is a schematic representation of a cornea with an anterior and posterior interface in myopia correction as well as with an indentation according to an exemplary embodiment.

In order to avoid these stresses, myopia correction is illustrated in FIG. 3 as it can be performed according to a preferred embodiment for controlling the eye surgical laser 12 of the treatment apparatus 10. In particular, at least one indentation 28 is provided, by which the arc lengths of the two interfaces are generated of equal length, in particular of equal length in all radial directions. Preferably, the indentation 28 can be arranged at a radially viewed outer part of the volume body 14 and extend radially around the volume body 14. Particularly preferably, the indentation 28 can be arranged in a transition zone of the volume body 14 such that an optical zone, which can be provided for correction with optical effect, is not influenced by the indentation 28. In case of myopia correction, it is preferably provided that the indentation 28 is generated in the shorter posterior interface 24 such that the arc lengths compensate for each other. In order that the indentation 28 elongates the posterior interface 24, it can preferably be provided that it is formed with an opposite direction of curvature to the posterior interface 24, thus the indentation 28 is concave to the convexly oriented posterior interface 24. Thus, it can be achieved that stresses in the cornea 16 can be reduced or avoided in myopia correction.

Figure 4:
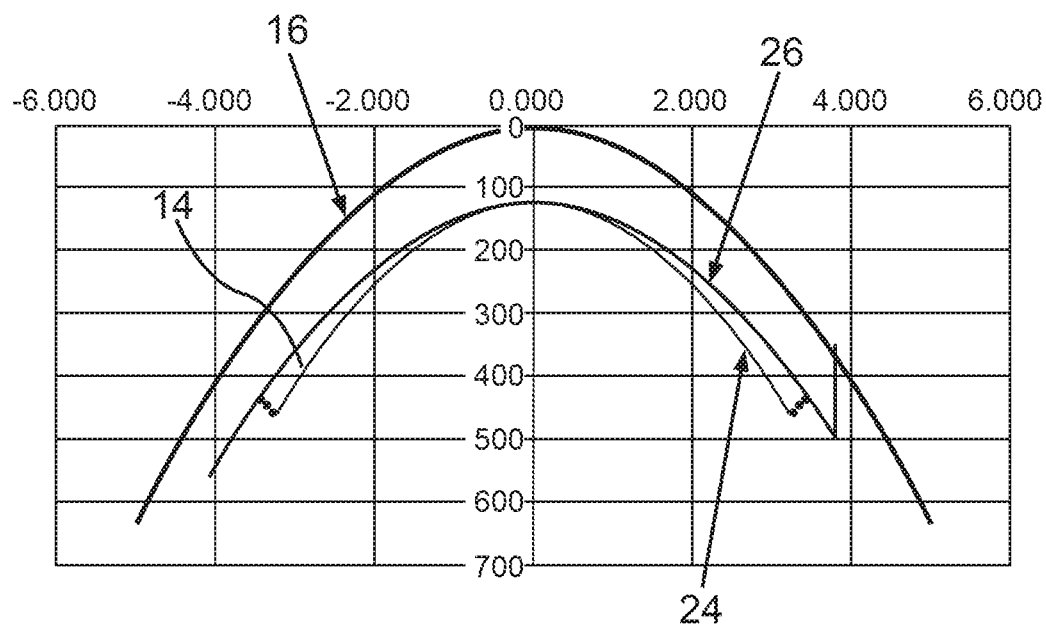
FIG. 4 is a schematic representation of a cornea with an anterior and posterior interface in hyperopia correction.

In FIG. 4, an exemplary representation of hyperopia correction is shown, in which the anterior interface 28 is formed flatter than the posterior interface 24. Hereby, it follows that the arc length of the posterior interface 24 is shorter than the arc length of the anterior interface 26, whereby stresses can arise in the cornea 16.

Figure 5:
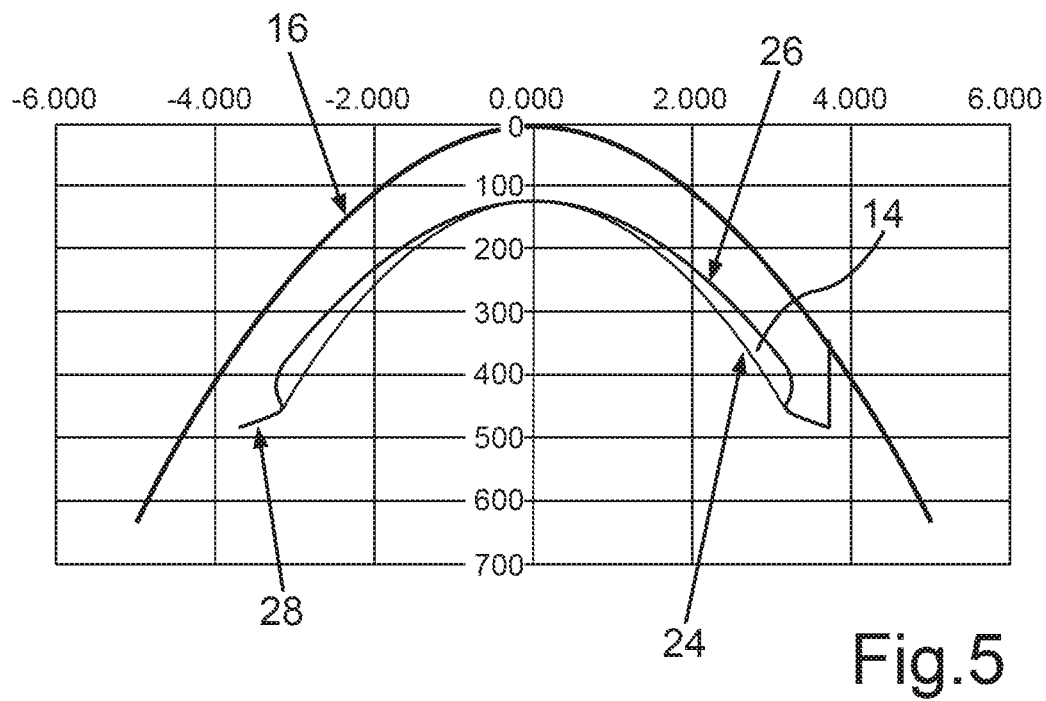
FIG. 5 is a schematic representation of a cornea with an anterior and posterior interface in hyperopia correction as well as an indentation according to an exemplary embodiment.

In FIG. 5, hyperopia correction is illustrated, as it can be performed according to a preferred embodiment for controlling the eye surgical laser 12 of the treatment apparatus 10 to compensate for the previously mentioned length difference of the arc lengths of the anterior interface 26 and the posterior interface 24. Herein, the indentation 28 can be generated in the anterior interface 26, whereby the shorter one of the two arc lengths is extended such that the arc lengths of both interfaces are equally long. Herein too, the indentation 28 can preferably be again generated in the transition zone of the volume body 14.

Thus, a transition zone can overall be provided, which compensates for a discrepancy, which is generated in an optical zone of the volume body 14, in that a new division of the tissue superposition is provided, which generates arc lengths with equal length. Hereby, better coincidences between the interfaces can be generated, which can result in shorter recovery times of the cornea 16.

What is claimed is:

1. A method for controlling an eye surgical laser of a treatment apparatus for the separation of a volume body with a predefined posterior interface and a predefined anterior interface from a human or animal cornea, comprising:
    controlling the laser by means of a control device of the treatment apparatus such that it emits pulsed laser pulses in a shot sequence in a predefined pattern into the cornea,
    wherein the interfaces of the volume body to be separated are defined by the predefined pattern and the interfaces are generated by means of an interaction of the individual laser pulses with the cornea by the generation of a plurality of cavitation bubbles, and
    wherein an arc length of the anterior interface and an arc length of the posterior interface are generated of equal length by means of at least one indentation in a shorter arc length of the anterior and the posterior interfaces.

2. The method according to claim 1, wherein the at least one indentation is generated at a radially viewed outer part of the volume body.

3. The method according to claim 1, wherein the volume body comprises an optical zone and a transition zone, wherein the at least one indentation is arranged in the transition zone.

4. The method according to claim 1, wherein if the separation of the volume body is performed for myopia correction, the at least one indentation is generated in the posterior interface.

5. The method according to claim 1, wherein if the separation of the volume body is performed for hyperopia correction, the at least one indentation is generated in the anterior interface.

6. The method according to claim 1, wherein if the separation of the volume body is performed for asymmetric correction, in particular astigmatism correction, the respective indentation is generated optionally in the anterior or posterior interface for a respective meridian of the volume body depending on the asymmetric correction.

7. The method according to claim 1, wherein the indentation is provided with a direction of curvature opposite to the curvature of the anterior and/or posterior interface.

8. A control device, which is formed to perform a method according to claim 1.

9. A treatment apparatus with at least one eye surgical laser for the separation of a volume body of a human or animal eye by means of photodisruption and/or photoablation, and at least one control device according to claim 8.

10. The treatment apparatus according to claim 9, wherein the laser is formed to emit laser pulses in a wavelength range between 300 nm and 1400 nm, at a respective pulse duration between 1 fs and 1 ns, and a repetition frequency of greater than 10 kHz.

11. The treatment apparatus according to claim 9, wherein the control device comprises
    at least one storage device for at least temporary storage of at least one control dataset, wherein the control dataset or datasets include(s) control data for positioning and/or focusing individual laser pulses in the cornea; and
    at least one beam device for beam guidance and/or beam shaping and/or beam deflection and/or beam focusing of a laser beam of the laser.

12. A computer program including commands, which cause a treatment apparatus with at least one eye surgical laser for the separation of a volume body of a human or animal eye by means of photodisruption and/or photoablation, and at least one control device to execute a method according to claim 1.

13. A computer-readable medium, on which the computer program according to claim 12 is stored.

14. A method for performing a surgical procedure on a human or animal cornea for the separation of a volume body with a predefined posterior interface and a predefined anterior interface,
    wherein for separating the volume body by an eye surgical laser of a treatment apparatus the interfaces are generated by means of an interaction of the individual laser pulses with the cornea by the generation of a plurality of cavitation bubbles, and
    wherein an arc length of the anterior interface and an arc length of the posterior interface are generated of equal length by means of at least one indentation in a shorter arc length of the posterior and anterior interfaces.

15. The method for performing a surgical procedure according to claim 14, wherein the at least one indentation is generated at a radially viewed outer part of the volume body.

16. The method for performing a surgical procedure according to claim 14, wherein the volume body comprises an optical zone and a transition zone, wherein the at least one indentation is arranged in the transition zone.

17. The method for performing a surgical procedure according to claim 14, wherein if the separation of the volume body is performed for myopia correction, the at least one indentation is generated in the posterior interface.

18. The method for performing a surgical procedure according to claim 14, wherein if the separation of the volume body is performed for hyperopia correction, the at least one indentation is generated in the anterior interface.

19. The method for performing a surgical procedure according to claim 14, wherein if the separation of the volume body is performed for asymmetric correction, in particular astigmatism correction, the respective indentation is generated optionally in the anterior or posterior interface for a respective meridian of the volume body depending on the asymmetric correction.

20. The method for performing a surgical procedure according to claim 14, wherein the indentation is provided with a direction of curvature opposite to the curvature of the anterior and/or posterior interface.

* * * * *